United States Patent [19]
Brown et al.

[11] Patent Number: 5,998,167
[45] Date of Patent: Dec. 7, 1999

[54] EXPRESSION CONTROL POLYNUCLEOTIDES DERIVED FROM SPLICEOSOMAL PROTEIN GENE PROMOTERS

[75] Inventors: John Willaim Slessor Brown, Perth; Gillian Patricia Clark, Angus; Gordon Grant Simpson, Norwich, all of United Kingdom

[73] Assignee: Scottish Crop Research Institute, Invergowrie, United Kingdom

[21] Appl. No.: 08/750,654

[22] PCT Filed: Jun. 19, 1995

[86] PCT No.: PCT/GB95/01443

§ 371 Date: Dec. 16, 1996

§ 102(e) Date: Dec. 16, 1996

[87] PCT Pub. No.: WO95/35386

PCT Pub. Date: Dec. 28, 1995

[30] Foreign Application Priority Data

Jun. 17, 1994 [GB] United Kingdom ............... 9412123
Jun. 17, 1994 [GB] United Kingdom ............... 9412124

[51] Int. Cl.$^6$ ............ C12P 21/02; C12N 15/11; C12N 15/63; C12N 5/04
[52] U.S. Cl. ............ 435/69.1; 435/91.4; 435/252.3; 435/254.11; 435/320.1; 435/325; 435/419; 536/23.1; 536/24.1; 536/24.5
[58] Field of Search ............ 435/69.1, 172.3, 435/320.1, 419, 91.41, 91.4, 252.3, 254.11, 325; 536/23.1, 24.1, 24.5

[56] References Cited

PUBLICATIONS

S.P.Jackson et al., Cloning of the RNA8 Gene of Saccharomyces Cervisiae, Detection of the RNA8 Protein, and Demonstration that it is Essential for Nuclear Pre–MRNA Splicing, J. Mol. Biol., vol. 8, No. 3, 1988, pp. 1067–1075.

G. Biamonti, et al., Two Homologous Genes, Originated by Duplication, Encode the Human HNRNP Proteins A2 and A1, vol. 22, No. 11, Jun. 11, 1994, pp. 1996–2002 Nucl. Acids. Res.

G. Biamonti, et al, Human HNRNP Protein A1 Gene Expression Structural and Functional Characterization of the Promoter, vol. 230, May 3, 1993, pp. 77–89 J. Mol. Biol.

J.I. Hamilton et al, Characterisation of a Gene Encoding the Spliceosmomal Protein PRP8 from Maize, Journal of Experimental Botany, vol. 46, no. suppl 1995, p. 38.

J.W.S. Brown et al, Plant Pre–MRNA Splicing and Splicing Components, Philosophical Transactions of London Biological Sciences, 342 (1301) 1993, pp. 217–224.

G.G. Simpson et al. Evolutionary Conservation of the Spliceosomal Protein, U2B, Nucleic Acids Research, vol. 19, No. 19, 1991, pp. 5213–5217.

H. Kulesza, et al., Detection of a Plant Protein Analagous to the Yeast Spliceosomal Protein PRP8. Febs Letters, vol.318, No. 1, Feb. 1993, pp. 4–6.

T. Kiss, et al. Molecular Analysis of a U3 RNA Gene Locus in Tomato; Transcription Signals, The Coding Region, Expression in Transgenic Tobacco Plants and Tandemly Repeated Pseudogenes, Nucleic Acids Research, vol. 18, No. 8, 1990, pp. 1941–1949.

D. Edoh, et al. Activity of U–SNRNA Genes with Modified Placement of Promoter Elements in Transfected Protoplasts and Stably Transformed Tobacco, Nucleic Acids Research, vol. 21, No. 7, 1993, pp. 1533–1540.

*Primary Examiner*—John S. Brusca
*Attorney, Agent, or Firm*—Ratner & Prestia

[57] ABSTRACT

An expression control polynucleotide capable of affecting the expression of a second polynucleotide, and derived from a spliceosomal protein gene promoter. Isolation of plant spliceosomal protein gene promoters from potato and maize is described. Partial sequences of the promoters of two potato spliceosomal protein gene promoters are disclosed.

28 Claims, 7 Drawing Sheets

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
         (A) LENGTH: 784 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Solanum tuberosum (xi) SEQUENCE DESCRIPTION: SEQ ID NO: 1:

```
TTAGAATTAG AATCCCCATT TTTAAGAATA ATCCTAGATA ATTTTCTTAA ACATGACAAT      60

TGATACCCAC AATTAATTAC TATTACATAA ATTTTTACCT AAATTAGATA TAACTTTCAA     120

TTTCAAAAAT TAAAACCCAA AAAAATTGAA CGACAATACG AGAGGGGATC AAACATAGGC     180

GAGCAATTAG AGAAATTGAC GGGTAGACAT CAACAAACCA TCAAGAATTT AAAAGCGGAA     240

AGAGAAAAAA ATACACTATG GACGAATATT TTTATAGAAT TCAATATGTA AAACTAATAA     300

ACAAGAAAGT AAATCATCTT TTATTCAAAG TAATGAAGAA GAAGAATTGA ATAAATATTT     360

ACATAATCAA TAAAAAAAAC TCATTCAAAA GAATCGTGTG TATGGGAAAG AAGAAGAAAA     420

AAAAGGCAGA AAAAAACCAC TTCCCAATAA AAAAGGACAT CATGCTGCCA CCTCCTAAAA     480

TTATTTAATT TAATTAAAAA AAAAACTTCC CAACACGTGG GCTACTAATT GCAAAATTTA     540

ATTTTTAAAA AGCTTTTTTT GTCAAGAAAA TAAAAGATGG CTATATGTTG CCAATTAGTA     600

AAATGGGATG TCATGCTGTG TCATTTTTTC TTGAGTTGTT AAGGGCTCAA AGCCCAATTG     660

TTTATCCAGC CCAAGCCCAA ATCGGAGCCC TATTCGTGCC CAAAAATTTC TGGAGAAATT     720

AACGACAACT GAAGTTTCTA CCTCACCGGC GAAAGTTGCA GCTAGGCGTA GACGAGGAGC     780

CATG                                                                 784
```

(2) INFORMATION FOR SEQ ID NO: 2:

(i) SEQUENCE CHARACTERISTICS:
         (A) LENGTH: 119 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Solanum tuberosum (xi) SEQUENCE DESCRIPTION: SEQ ID NO: 2:

```
TCTCTCCAGC TCTTCCCTCC TAAAACAACC ATTTTATGAG TACAGACACA AACCAGCTTA      60

GCAACCAGTA AATCCAAAAC TTTAATTCCA CGTGTAAGCG CTAACACTTC ACCCACTAA      119
```

(2) INFORMATION FOR SEQ ID NO: 3:

(i) SEQUENCE CHARACTERISTICS:
        (A) LENGTH: 139 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Solanum tuberosum (xi) SEQUENCE DESCRIPTION: SEQ ID NO: 3:

```
TCTTTACACT ATTTTCAAAT AACGATGAGA CCTGTAATAA TGTAATAACT TGAAAATAGA      60

ACAATAACTC ATTCAGTACA ACAAATAAAA TCATACTAAT GTATATTTTT AAAAACAATT     120

TAACTCTATT TAATTAATC                                                  139
```

(2) INFORMATION FOR SEQ ID NO: 4:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Solanum tuberosum (xi) SEQUENCE DESCRIPTION: SEQ ID NO: 4:

```
ATATCTAAAA AAATGTGATT GGAGCACTCA TTGACCACAC GAATGAATCT ACAATGTAGA      60

TCATTCTATC TAGACAAATA ATGCAAAAAC TAAAAGATAA AAGTAATATT ATACTACAAT     120

CTGTTAAATG ATATCAATAT TACAAAAGTT CTCTACGATG TCAATACATA TATTAAAATC     180

TATTTGATTA ATCAGAAACA TATCATGTGT GAATTTTTTT AATTAAAGAT CCCTTTAATC     240

ATCTGAATCA ACCTTGGCTG GTCTCACATC TTTCCACCCT CTACTCGGTC TTCACTTTCT     300

CTTAAACTAG GGAAGAACAA CATGATATTA GCTTAGATTA ATTAAACAAG CTCATCAAAA     360

CTACCATCCA ATTTAAGCCA ATAATGTTTA AATAAAACAA AAAACAACGT ACTCATTTTT     420

TCATAACAAG AAGTTAAAAT TTATATGAAT CCTTACTCCA AAAAAGAAGA AAAATTACAA     480

TATCAATATA TATAACTACT CTATTTGGTT AGTCAACAAA ATGTTAGTAT ATGTATTGCA     540

AGTTCGCAAC ACCCGCTTGG GCCTTGACCA CATATTTATA TGGGCCGGTT GTCAATTTAA     600

GCCCACTTTG TGTTCGTTCG CCTTTCTTGT AGCTCCAAAC TCTTGGAAAT TTGTCGAGCA     660

CATTCAGAAA TCACAGAGAA GAGCAAGTGA ATATACATAC AGATAGAGAA AAGCTGCTCT     720

GCTCGGTAAT G                                                         731
```

EXPRESSION CONTROL POLYNUCLEOTIDES DERIVED FROM SPLICEOSOMAL PROTEIN GENE PROMOTERS

This invention relates to expression control polynucleotides derived from spliceosomal protein gene promoters.

It is already well known that organisms such as plants or animals with novel characteristics can be produced by introducing genes or DNA sequences from the same or a related organism or by introducing genes or DNA sequences from other organisms. The key to production of novel phenotypes is the active expression of at least a part of the introduced DNA sequence. Generally expression of the introduced DNA sequence will occur only in the presence of an expression control polynucleotide, such as a promoter, which is compatible with the host organism. Promoters are nucleic acid sequences which are currently believed to regulate the expression of a gene by facilitating the binding of proteins required for transcription, such as RNA polymerase, to a portion of the nucleic acid sequence upstream of the gene. Thus for protein coding genes the DNA is transcribed into mRNA (messenger RNA) which is then relocated to the cytoplasm where it is available for translation into polypeptide.

Whereas promoters are generally disposed upstream of the genes they regulate and are thought to act by providing a binding site for an RNA polymerase transcription complex, another form of expression control polynucleotide known as an "enhancer" sequence can control the expression of a gene usually without regard to its relative position or orientation.

Promoters can vary in levels of expression induction and in their expression patterns. Some promoters are active in a tissue-specific or developmental stage-specific manner while other promoters are active constantly to continually drive expression of the gene they control. Such constantly active promoters are called constitutive promoters. The promoters of this latter class most widely used in genetic engineering are the Cauliflower Mosaic Virus (CaMV) 35S RNA promoter, nopaline synthetase (nos) or octopine synthetase (ocs) promoters. Constitutive promoters induce gene expression at a relatively constant rate.

Although the above conventional promoters generally drive expression at high levels, many have the disadvantage that they are derived from plant infectious agents; the CaMV 35S RNA promoter is derived from a plant virus and the other promoters mentioned are derived from strains of Agrobacterlium, soil-borne infectious bacteria. The source of these promoters is a cause of concern in transgenic plant production. In addition, detailed analysis of expression patterns of CaMV 35S promoter, have shown that its levels of expression can vary greatly among different plant tissues to the level where it is inactive in some tissues and is therefore, no longer constitutive for such tissue. For many biotechnological objectives, constitutive expression in all cells and tissues would be of great advantage.

Splicesomal proteins are believed to be present in virtually all eukaryotic cells and are involved in the phenomenon of pre-mRNA splicing which removes introns (non-coding regions) from RNA transcripts before protein production.

The present invention seeks to provide a promoter (or other expression control polynucleotide) which is not derived from an infectious agent and which is suitable for use in the control of expression of recombinant genes in the construction of transgenic organisms such as plants and animals.

The present invention also seeks to provide a promoter (or other expression control polynucleotide) which is likely to be active throughout all or most cells of the organism.

According to the present invention there is provided an expression control polynucleotide at least partially derived from a spliceosomal protein gene promoter.

The expression control polynucleotide of the invention is capable of controlling the expression of a second polynucleotide (preferably comprising a polypeptide-encoding sequence) operably linked thereto.

RNA sequences which do not code for protein can also be expressed eg ribozymes or anti-sense RNA.

The term "expression control polynucleotide" as used herein will include promoters, enhancers or any other functional equivalents or any other sequence elements which affect expression of other gene sequences.

The term "polypeptide-encoding sequence" as applied herein to polynucleotides means a polynucleotide comprising a sequence which can be transcribed into mRNA, which itself can be translated into a polypeptide. The "polypeptide-encoding sequence" may include non-translated portions, such as introns.

The spliceosomal protein gene promoter may be derived from plants. The plants may be dicotyledonous (eg potatoes), or monocotyledonous (eg maize).

The present invention also provides a recombinant polynucleotide comprising an expression control polynucleotide according to the invention operably linked to a second polynucleotide (preferably comprising a polypeptide-encoding sequence).

The present invention also provides a recombinant vector containing an expression control polynucleotide or a recombinant polynucleotide as defined above.

According to the present invention there is also provided a method of producing a recombinant vector, said method comprising ligating an expression control polynucleotide into a vector or part thereof. A method of producing a transformed cell by transfecting a host cell using said recombinant vector forms another aspect of the invention.

The present invention also provides a transformed host cell containing a recombinant polynucleotide or vector as defined above.

The present invention also provides a transgenic organism (for example a transgenic plant) containing a recombinant polynucleotide or vector as defined above. The progeny (and seeds) of such transgenic organisms forms a further part of the invention.

The present invention also provides a method for controlling the expression of a polypeptide from a nucleotide sequence encoding the polypeptide, said method comprising operably linking said sequence to an expression control polynucleotide of the invention.

The expression control polynucleotide of the invention may comprise double- or single-stranded DNA or RNA.

Three cultures of *E.coli* (SCRI/JB/1, SCRI/JB/2 and SCRI/JB/3), each containing a plasmid having an expression control polynucleotide according to the invention were deposited on Mar. 14, 1994 with the National Collection of Type Cultures under numbers NCTC 12864, NCTC 12865 and NCTC 12866 respectively.

Cultures SCRI/JB/1 and 2 contain dicotyledonous spliceosomal protein gene expression control polynucleotides (promoters for potato U1A and U2B" genes respectively); SCRI/JB/3 contains a monocotyledonous expression control polynucleotide (promoter for a maize PRP8 gene).

Accordingly, the present invention also provides NCTC deposits Nos 12864, 12865 and 12866 and the plasmids thereof.

Recombinant DNA technology has been recognised as a powerful technique not only in research but also for commercial purposes. Thus, by using recombinant DNA techniques (see Sambrook et al 1982 and "Principles of Genetic Engineering", old and Primrose, 5th edition, 1994) exogenous genetic material can be transferred to a host cell and the polypeptide encoded by the exogenous genetic material may be replicated by and/or expressed within the host. For the purposes of simplicity recombinant DNA technology is normally carried out with prokaryotic micro-organisms, for example bacteria such as *E. coli*, as host. However, use has also been made of eukaryotic organisms, in particular yeasts or algae, and in certain applications eukaryotic cell cultures may also be used.

Genetic alterations to mammalian species by microinjection of genes into the pro-nuclei of single-cell embryos is also well known and has been described by Brinster et al, in Cell 27: 223–231, 1981. Thus general techniques used in recombinant DNA technology and the production of transgenic organisms is within the scope of the skilled man.

Using a cDNA sequence (complimentary DNA—reverse transcribed from mRNA), either full-length or partial, as a probe for a gene of interest, the gene promoter can be readily isolated by standard procedures. Briefly, the cDNA probe is first used to screen a genomic library to isolate a genomic clone containing the promoter and coding sequence. Restriction mapping and Southern blotting with the cDNA as probe delineates the region of the genomic clone containing the coding sequence. Sequencing of this region of the genomic clone and comparison to the cDNA clone will identify the translation initiation ATG codon, and if the cDNA is full-length, will give an indication of the transcription start site, upstream of which lies the gene promoter. Important promoter sequence elements may lie in excess of around 2 kbp of the transcription start site. Therefore, a genomic fragment of preferably 1–5 kbp is isolated for initial testing of promoter activity. For example, in the case of U1A and U2B", a monoclonal antibody (mAb), 4G3, raised against a b-galactosidase-human U2B" protein, was used as a probe to screen a potato cDNA expression library and a full-length cDNA clone was isolated (Simpson et al. 1991). Screening of a potato genomic library using this cDNA clone resulted in a genomic clone containing part of the gene and around 15 kbp upstream sequences which were used to clone the promoter in subsequent experiments. The extreme similarity between U1A and U2B" enabled us to isolate a full-length genomic clone of the U1A gene. Since the latter clone contained around 7 kbp of upstream sequences, it was possible to clone the promoter from the upstream region.

The use of spliceosomal protein gene promoters to drive expression of DNA sequences in transgenic plants or animals has the advantage that the expression is constitutive, expressed in all cell and tissue types and uses naturally occurring plant or animal nucleic acid sequences which are not derived from infectious agents.

While further modifications and improvements may be made without departing from the scope of this invention, the following is a description of one or more examples of the invention, with reference to the accompanying drawings, in which.

EXAMPLE 1

Genes for two plant spliceosomal proteins from the dicotyledonous plant, potato (*Solanum tuberosum*) were isolated encoding the spliceosomal proteins U1A and U2B".

The promoter of a potato U2B" gene was isolated from a potato genomic library in λ EMBL 3 by conventional methods. The library was screened with a potato U2B" cDNA clone (Simpson et al., 1991) using standard procedures (Sambrook et al., 1989). The potato U2B" genomic clone was plaque-purified, DNA prepared, fragments subcloned into plasmid vectors and DNA sequenced by standard procedures (Sambrook et al. 1989).

Figure 1:
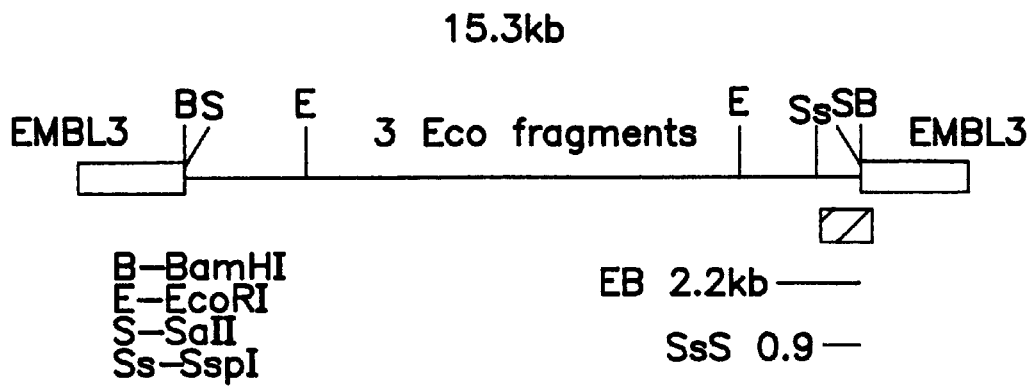
FIG. 1 shows a schematic diagram of a potato U2B" genomic clone present in the cells of culture No SCRI/JB/2.

The genomic clone contained an insert of 15 kilobase pairs (kbp) (FIG. 1) from which relevant sub-fragments were cloned into plasmid vectors (FIG. 1). The clone only contained a fragment of coding region of U2B" (100 bp), a fragment of the first intron in U2B" (100 bp) and approximately 15 kbp of upstream sequences containing the U2B" promoter.

EXAMPLE 2

Figure 2:
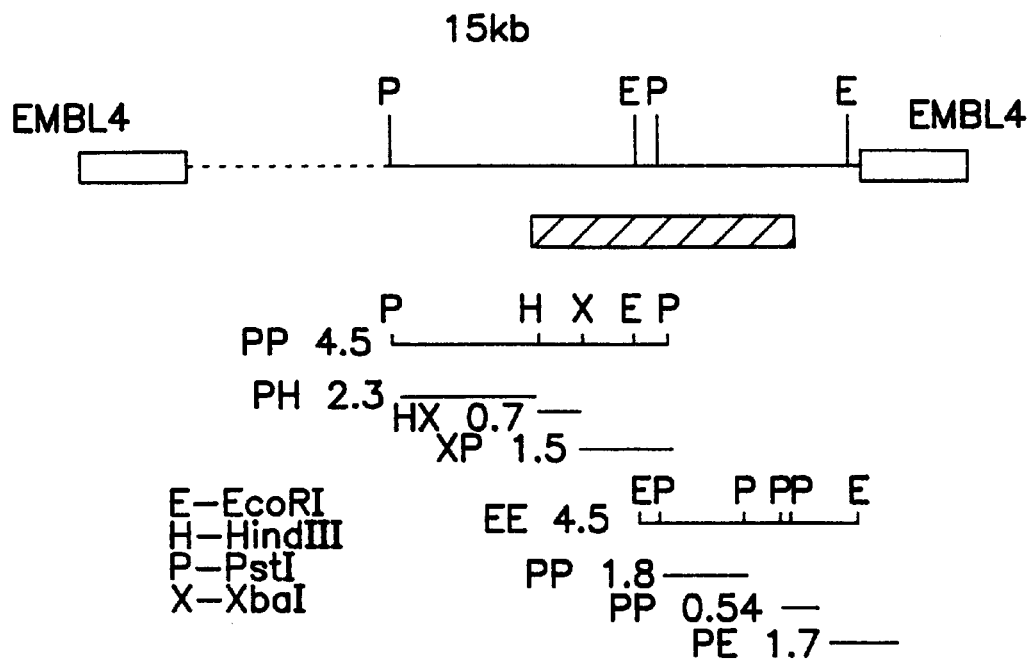
FIG. 2 shows a schematic diagram of a potato U1A genomic clone present in the cells of culture No SCRI/JB/1.
Figure 3:
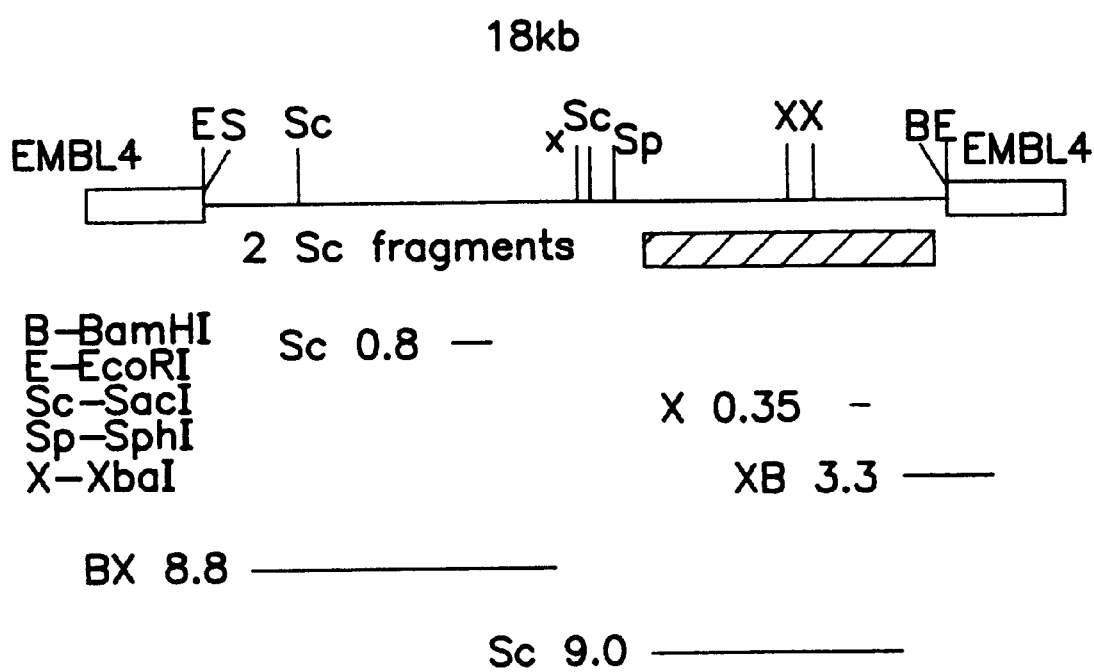
FIG. 3 shows a schematic diagram of a maize PRP8 genomic clone present in the cells of culture No SCRI/JB/3.

The promoter of a potato U1A gene was isolated from a potato genomic library in λ EMBL 4. The library was screened with a potato U2B" cDNA clone (Simpson et al., 1991) because U1A and U2B" are closely related, and a genomic clone was obtained by known methods. The genomic clone was characterised by state-of-the-art methodologies as described by Sambrook et al., (1989). The clone contained an insert of 15 kbp (FIG. 2) from which relevant sub-fragments were cloned into plasmid vectors by standard techniques (Sambrook et al., 1989). The clone contained the whole of the U1A coding sequence on five exons, four introns and 7 and 2 kbp of 5' and 3' flanking sequence respectively.

The promoter regions can be linked to marker genes such as bacterial β-glucuronidase (Jefferson, 1987) by standard molecular techniques (Sambrook et al., 1989). Promoter constructs can be analyzed by introduction into plant cells by known methodology such as chemical or electrical transfection, microinjection, biolistics or Agrobacterium-mediated or other vector-mediated transformation (see Shaw, 1988). Transgenic plants containing the construct can be analyzed by detecting the presence of GUS enzyme and thereby its expression using known methods of histochemical staining (Jefferson, 1987). Levels of expression of marker genes driven by the promoters in either stably transformed plants or transiently transformed plant cells or protoplasts can be assessed by comparison with levels of endogenous gene expression and of marker gene expression driven by the Cauliflower Mosaic Virus 35S RNA promoter. This analysis can use known, state-of-the-art methodologies to detect RNA transcripts (Sambrook et al., 1989; Simpson et al., 1992) and to detect production of enzyme from marker genes, for example, for GUS marker gene activity.

The promoter region can be incorporated into plasmid vectors designed for general use in construct production in E.coli, and for use in stable, Agrobacterium-mediated transformation and in transient transformation or stable, physical transformation methods. DNA sequences to be expressed in the transgenic plant can be inserted behind the promoter regions as is currently commonly performed using the CaMV 35S RNA promoter (see Shaw, 1988) prior to introduction into plant cells or production of transgenic plants.

EXAMPLE 3

A gene for a plant spliceosomal protein was cloned from the monocotyledonous plant, maize (Zea mays L.), which encodes the spliceosomal protein PRP8 (Jackson et al., 1988) by virtue of sequence homology to PRP8 of yeast.

The genomic clone of maize PRP8 was isolated from a maize genomic library constructed in λ EMBL 4 by conventional methods. The library was screened with a fragment of maize PRP8 generated by state-of-the-art methodologies, such as polymerase chain reaction (PCR) amplification using oligonucleotide sequences designed from the yeast and Caenorhabditis elegans PRP8 DNA sequences, cloning and sequencing. The maize PRP8 genomic clone was plaque purified, DNA prepared and fragments subcloned into plasmid vectors by standard procedures.

The PRP8 promoter region can be incorporated into plasmid vectors as previously described.

EXAMPLE 4

Promoter/GUS Constructions

Two expression cassettes containing the β-glucuronidase (GUS) gene driven by the potato U1A and U2B" splicesomal protein gene promoters respectively were constructed. Both cassettes contained the nopaline synthase poly A (NOS-ter) downstream to the GUS gene. The construction of these expression cassettes was achieved by replacing the CaMV 35S promoter in the vector pBI221 by upstream sequences of the potato U1A and U2B" spliceosomal protein genes. Genomic clones described above were used.

U1A

Figure 4:
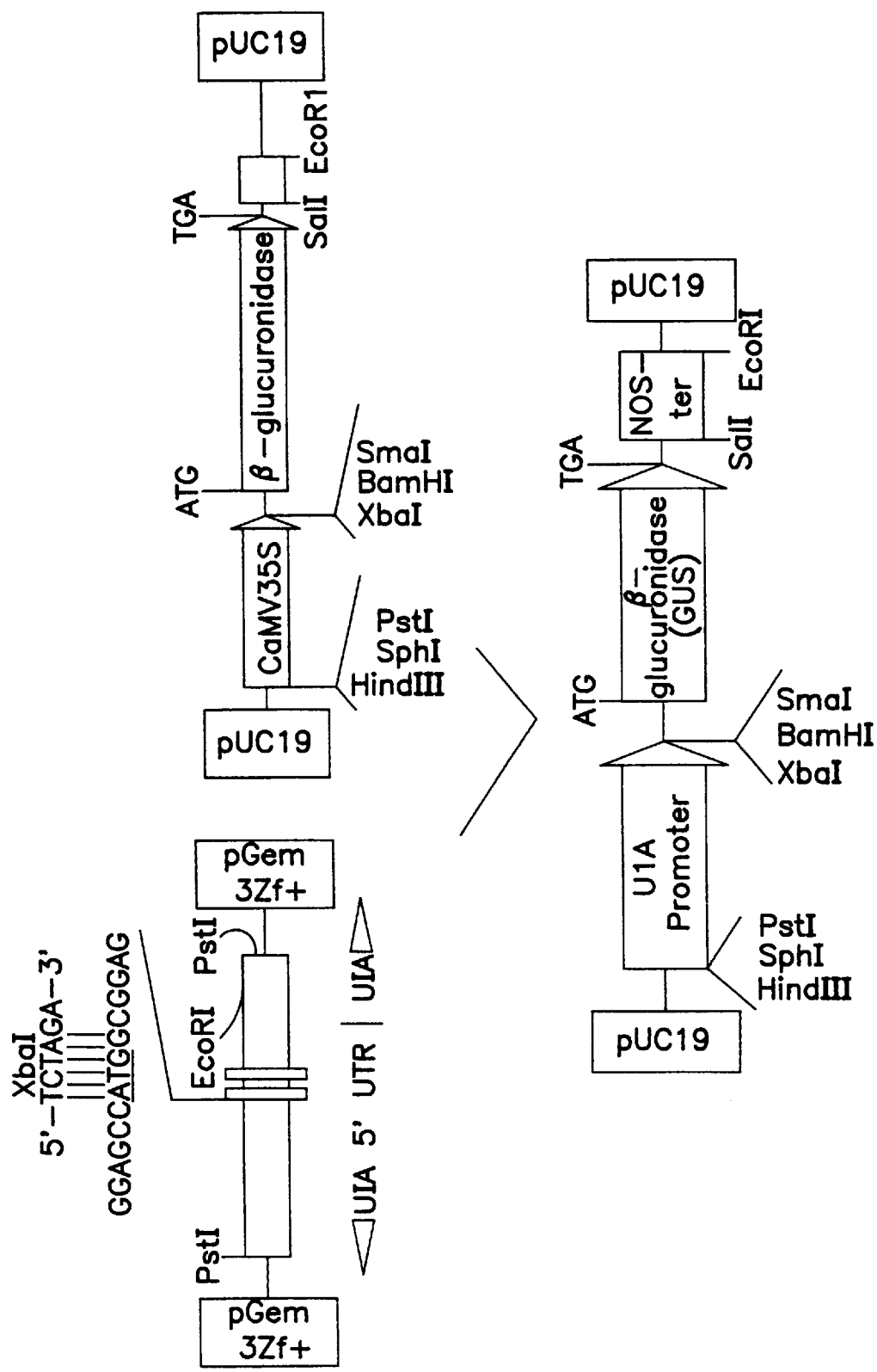
FIG. 4 shows a schematic diagram of a U1A/GUS expression cassette.

A 4.5 kb PstI fragment containing about 2.5 kb upstream to the U1A gene, the first and the second exons, the first intron and part of the second intron was used to clone the U1A promoter. In order to clone the promoter, a site specific mutation was generated which changed the sequence ATG-GCG at the translation start site into TCTAGA to introduce an XbaI restriction site. Subsequently, the entire 2.5 kb upstream region was cloned into pBI221 after eliminating the 35S promoter using the restriction enzymes PstI and XbaI (FIG. 4).

U2B"

Figure 5:
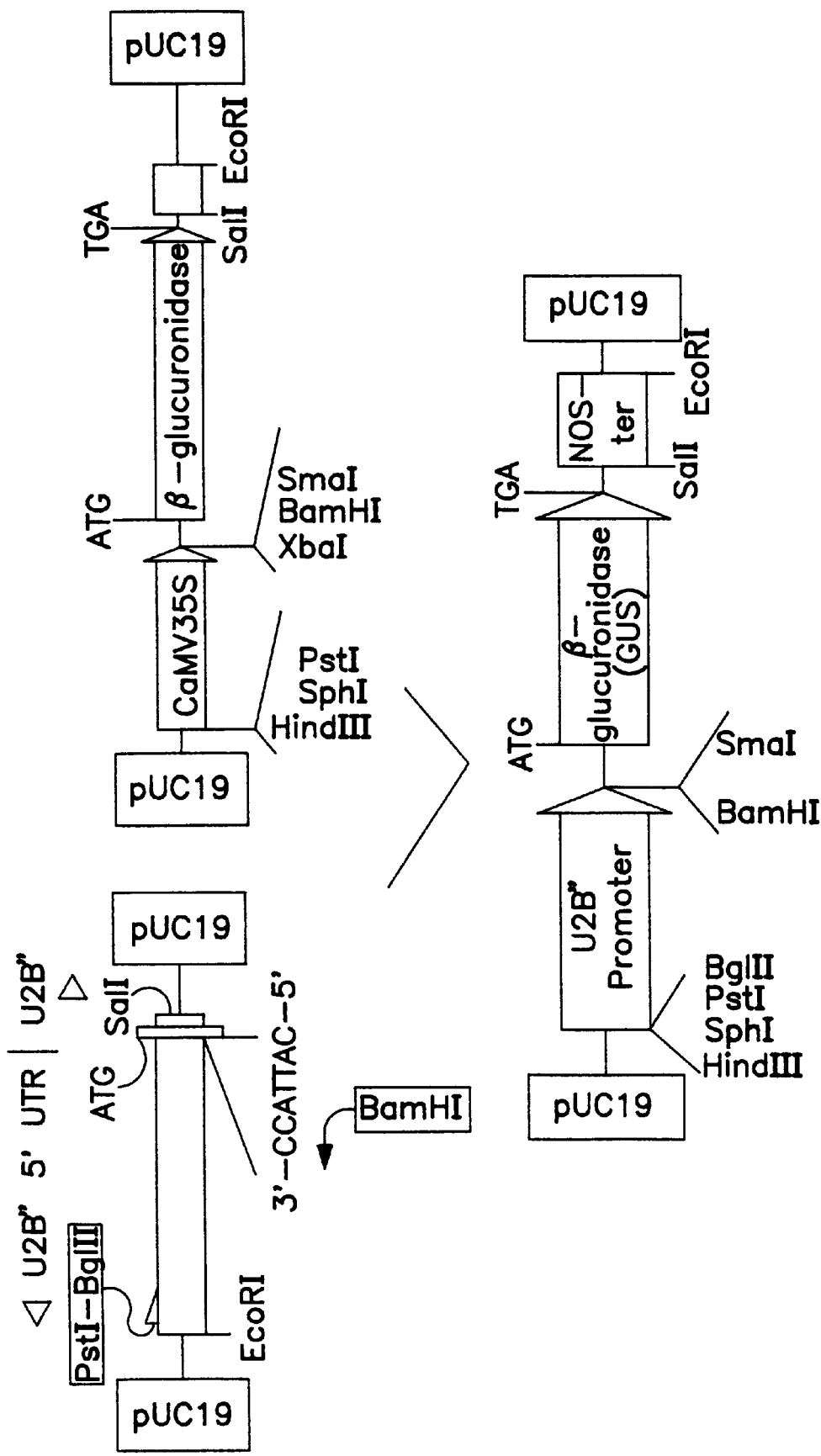
FIG. 5 shows a schematic diagram of a U2B"/GUS expression cassette.

An EcoRI/SalI fragment containing about 2 kb upstream to the U2B" gene, the entire first exon, and part of the first intron was used to clone the U2B" promoter. Appropriate restriction sites were introduced into the upstream region using PCR amplification. The first PCR primer started a few nucleotides downstream of the EcoRI site and contained additional nucleotides in its 5' end to provide PstI and BglII sites. The second primer started two nucleotides upstream of the ATG start codon and contained additional nucleotides providing a site for cleavage by BamHI at its 5' end. After PCR amplification and digestion with BamHI and PstI, the 2 kb upstream region was cloned into pBI221 replacing the 35S promoter (FIG. 5).

Protoplast Isolation

The constructed cassettes were tested for promoter activity in transient gene expression assays using tobacco protoplasts. Protoplasts were prepared from young, fully expanded tobacco leaves. Leaves were placed in 7% Domestos for 10 minutes, washed with sterile tap water, dried, and peeled to remove the lower epidermis. Peeled leaf pieces were placed onto 15 ml enzyme solution in a sterile Petri dish [enzyme solution: 1 mg/ml cellulase, 0.5 mg/ml driselase, 0.2 mg/ml macerase, suspended in TO$^-$ (see appendix)] and incubated overnight in the dark at 25° C. Protoplasts were transferred into two sterile 10 ml tubes through sterile sieves and spun at 400 rpm for 5 minutes. After resuspending each protoplast pellet in 10 ml TO$^-$, 5 ml aliquots were each layered onto 2.5 ml 16% sucrose and spun at 800 rpm for 5 minutes. The purified protoplasts were resuspended in 10 ml TO$^-$, spun at 400 rpm for 5 minutes, and recollected in 5 ml TO$^-$.

Protoplast Transfection

Transfection of the protoplasts with the U1A/GUS and U2B"/GUS constructs was achieved using plasmid DNA purified by Qiagen (Trade Mark) columns. For each experiment 200 μl of the purified protoplasts were transfected with 30 μg DNA dissolved in 20 μl distilled water. After dropwise addition of the DNA and careful homogenization of protoplasts, 200 ml of PEG solution was added. [PEG solution: 25% PEG 8000, 0.1M Ca(NO$_3$)$_2$, 0.45M Mannitol, 10 mM MES: 2-(N-Morpholino) ethanesulfonic acid] was added dropwise. The transfected protoplasts were then incubated at ambient temperature for 20 minutes; subsequently, 4 ml calcium nitrate was carefully added [0.275 M Ca(NO$_3$)$_2$]. After an incubation period of 20 minutes at ambient temperature protoplasts were spun at 400 rpm for 3 minutes, suspended, and resuspended in 5 ml TO$^+$. The transfected protoplasts were then incubated in sealed Petri dishes in the light at 25° C. for 48 hours.

GUS Assays

Samples were collected by spinning the protoplasts at 400 rpm for 3 minutes, resuspended, transferred into Eppendorf tubes (1 ml each), and spun again at 1000 rpm for 2 minutes in a cold microcentrifuge (4° C.). The pellet was then resuspended in 200 μl extraction and reaction buffer (50 mM NaPO$_4$ pH 7.0, 10 mM EDTA, 0.1% Triton X-100, 10 mM β-mercaptoethanol), spun at 1300 rpm for 3–5 minutes, and the supernatant was stored in clean Eppendorf tubes. 50 μl sample extract was added to 220 μl extraction and reaction buffer in an eppendorf tube and preincubated at 37° C. for 5 minutes. At 15 sec intervals, 30 μl 1 mM MUG (4-methyl umbelliferyl glucuronide) substrate was added to each tube giving time to stop reactions at accurate intervals. At defined time points, 100 μl samples were taken and added to 2.9 ml stop solution (0.2 M Na$_2$CO$_3$) in a clean cuvette. At this stage, GUS activity could be inspected visually by transillumination using a long wave UV light box. Quantitative measurements of fluorescence were made using a fluorometer. Protoplast transfections and GUS assays have been performed to investigate the expression of the GUS gene driven by splicesomal protein gene promoters using the above described constructs. In all experiments, the vector pBI221 which contains the GUS gene driven by the CaMV 35S promoter and terminated by the nopaline synthase poly A was used as a positive control. Negative controls were a: extracts from protoplasts transfected with water instead of plasmid DNA; and b: MUG substrate added to the extraction and reaction buffer without the addition of any extracts.

Figure 6:
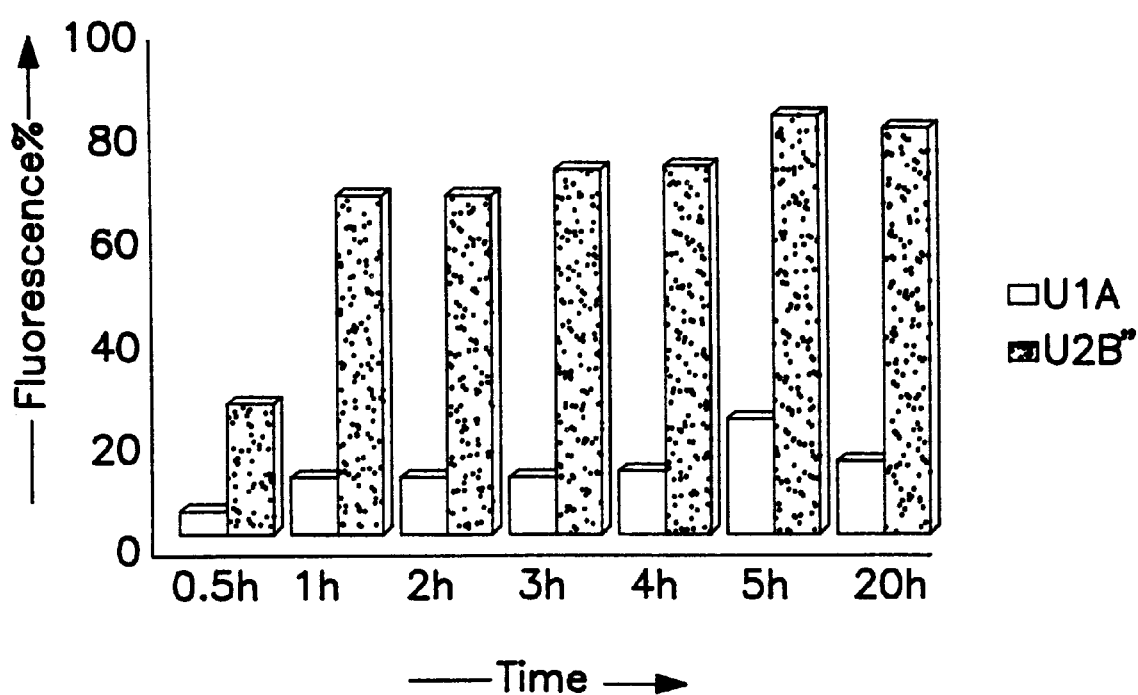
FIG. 6 shows a graph of fluorescence against time plotted from data collected from a fluorometric assessment of GUS gene expression controlled by potato spliceosomal protein gene promoters.
Figure 7:
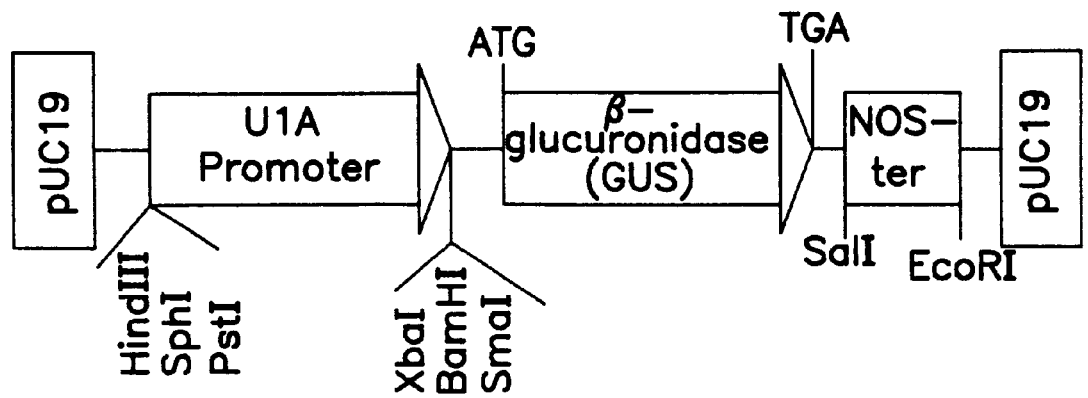
FIG. 7 shows a schematic diagram of a U1A/GUS expression cassette.
Figure 8:
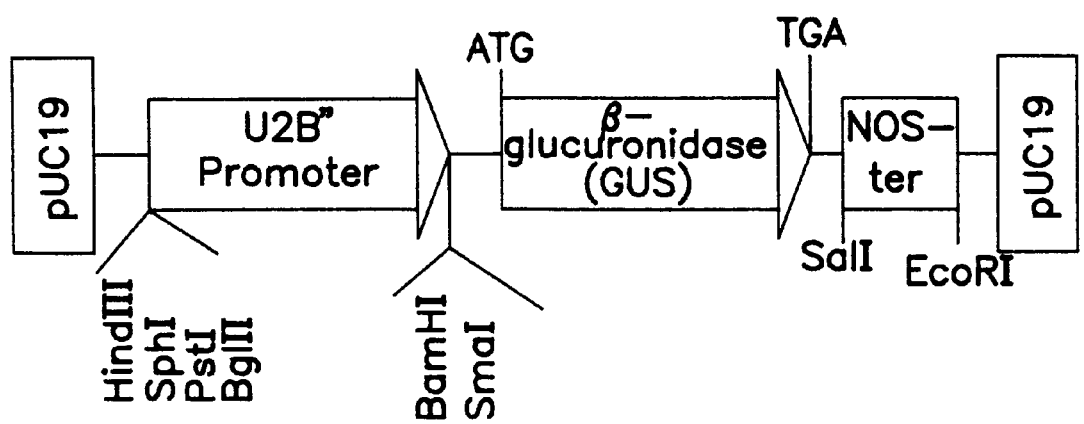
FIG. 8 shows a schematic diagram of U2B"/GUS expression cassette.

Reactions were carried out for 30 minutes, 1 hour, 2 hours, 3 hours, 4 hours, 5 hours and 20 hours. In order to assess the activity of the tested promoters in comparison to the 35S promoter, fluorometer readings were set at 100 for pBI221 at each time point so that the readings obtained for U1A and U2B" indicated the GUS activity in each case relative to that obtained for the 35S promoter. The results which are illustrated in FIG. 6 show that the U2B" promoter has about 70% of the activity of the 35S promoter whereas the U1A promoter gave rise to 10–15% of the activity observed for the 35S promoter.

Figure 9:
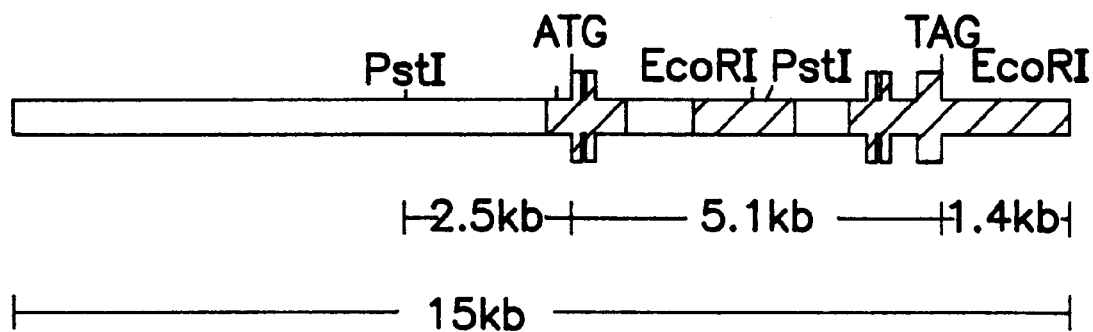
FIG. 9 shows a schematic diagram of the genomic organisation of the potato U1A gene.
Figure 10:
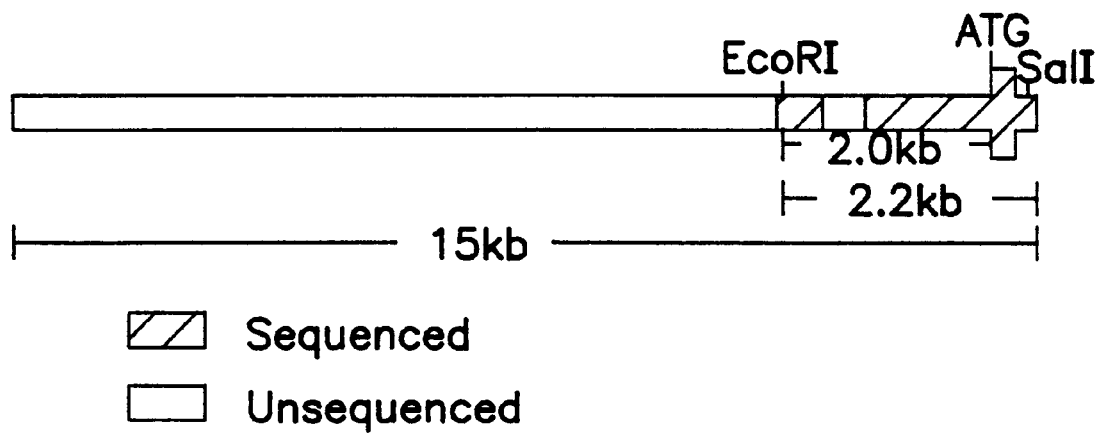
FIG. 10 shows a schematic diagram of the genomic organisation of the potato U2B" gene.

FIGS. 9 and 10 show the genomic organisation of the original genomic clones made of potato genes U1A and U2B". The promoter of the U1A gene is believed to lie in the region between the ATG initiation codon and the PstI site 2.5 kb upstream of the coding sequence initiating at the ATG start codon. The promoter of the U2B" gene is believed to lie in the region between the ATG coding region and the EcoRI site 2.0 kb upstream of the coding sequence initiated by the ATG start codon.

FIGS. 9 and 10 indicate regions of the genomic clones containing the promoters of U1A and U2B" which have been sequenced. The sequences of those regions are shown in the sequence listing.

The partial U1A promoter sequence is shown on the sequence listing as SEQ:ID:No1. Sequence data is presented for the 3' end of the region between the ATG codon and a Pst1 site 2.5 kb upstream. About 1.7 kb of the 5' end of this region has not been sequenced. The partial sequence of the U2B" genomic clone is shown in the sequence listing as three separate sequences since incomplete sequence data is available for this promoter. The first of the U2B" sequences shown is SEQ:ID:No2 which corresponds to the region from the 5' end TCT to a TAA 119 bases downstream. After the 3' end of SEQ:ID:No2 there is a region of approximately 900 bases which have not been sequenced. After the 3' end of the 900 bp unidentified region, the next U2B" sequence portion available is SEQ:ID:No3 which runs from a TCT approximately 900 bases downstream of the end of SEQ:ID:No2 to an ATC a further 139 bases downstream. After the 3' end of SEQ:ID:No3 there is a region of 11 bases which have not been identified. This unidentified region is followed by the last sequenced portion of the U2B" clone which is designated as SEQ:ID:No4 which starts at ATA at its 5' end and ends at the ATG codon (bases 729–731) initiating transcription of the coding region of U2B" (not shown).

Spliceosomal protein gene promoters (or other expression control polynucleotides) have the advantages that (a) spliceosomal proteins are absolutely required and thus spliceosomal protein gene promoters are likely to be active in every cell and tissue type; (b) they are not derived from infectious agents which overcomes objections to the use of such sequences due to potential recombination; and (c) different genes or DNA sequences are likely to be expressed at different levels reflecting the relative abundance of the different spliceosomal proteins.

Modifications and improvements may incorporated without departing from the scope of the invention. For example, an expression control polynucleotide in accordance with the invention may be operably linked to a second polynucleotide which has some function other than coding for a polypeptide. One such example might be to operably link an expression control polynucleotide to a gene encoding a ribozyme or anti-sense RNA. Indeed it will be realised by the skilled man that the function of the gene under the control of the expression control polynucleotide of the invention is not important, and that the expression of many diverse genes can be controlled.

References

The following references are incorporated herein by reference.

Jackson, S. P., Lossky, M & Beggs, J. D. (1988). Mol Cell Biol. 8, 1067–1075.

Jefferson, R. A. (1987). Assaying chimaeric genes in plants: the GUS gene fusion system. Plant Molecular Biology Reporter 5, 387–405.

Simpson, G. G., Vaux, P., Clark, G., Waugh, R., Beggs, J. D. & Brown, J. W. S. (1991). Evolutionary conservation of the spliceosomal protein, U2B". Nucleic Acids Research 19, 5213–5217.

Simpson, C. G., Sinibaldi, R. & Brown, J. W. S. (1992). Rapid analysis of plant gene expression by a novel reverse transcriptase-PCR method. Plant Journal 2, 835–836.

Sambrook, J., Fritsch, E. F. & Maniatis, T. (1989). Molecular Cloning—A Laboratory Manual. Cold Spring Harbor Laboratory Press, Cold Spring Harbor, N.Y.

Shaw, C. H. (1988). Plant molecular biology: a practical approach. IRL Press.

APPENDIX 1

| TO– | TO+ |
|---|---|
| 4 ml solution 1 | 4 ml solution 1 |
| 200 ml solution 3 | 4 ml solution 2 |
| 200 ml solution 4 | 200 ml solution 3 |
| 200 ml NAA (3 mg/ml) | 200 ml solution 4 |
| 200 ml BAP (1 mg/ml) | 200 ml NAA (3 mg/ml) |
| 16 g Mannitol | 200 ml BAP (1 mg/ml) |
| pH 5.5 adjusted with NaOH | 16 g Mannitol |
| filtersterilised +200 ml | 4 g Sucrose |
| cefotaxime (100 mg/ml) | 40 ml Tween 20 |
|  | pH 5.5 adjusted with NaOH |
|  | filtersterilised +200 ml |
|  | cefotaxime (100 mg/ml) |
| Solution 1 | Solution 2 |
| 10.30 mM $NH_4NO_3$ | 100 μM $FeSO_4$ |
| 9.40 mM $KNO_3$ | 100 μM $Na_2$ EDTA |
| 1.50 mM $CaCl_2 2H_2O$ |  |
| 0.75 mM $MgSO_4.7H_2O$ |  |
| 0.62 mM $KH_2PO_4$ |  |
| Solution 3 | Solution 4 |
| 16.00 μM $H_3BO_3$ | 555.00 μM Inostol |
| 0.60 μM $MnSO_4.H_2O$ | 3.00 μM Thiamine |
| 3.50 μM $ZnSO_4.7H_2O$ | 5.00 μM Pyridoxine |
| 0.12 μM $CuSO_4.5H_2O$ | 8.00 μM Niacin |
| 0.22 μM $AlCl_3$ | 2.00 μM Pantothenate |
| 0.13 μM $NiCl_3.6H_2O$ | 0.04 μM Biotine |
| 0.06 μM KI | +1 mg/μl NaOH |

We claim:

1. An isolated polynucleotide comprising a spliceosomal protein gene promoter of a plasmid in a cell line deposited as any one of NCTC 12864, NCTC 12865, or NCTC 12866.

2. A recombinant polynucleotide comprising the spliceosomal protein gene promoter according to claim 1.

3. A recombinant vector comprising the spliceosomal protein gene promoter according to claim 1.

4. A host cell transformed with the spliceosomal protein gene promoter as claimed in claim 1.

5. A host cell comprising the recombinant polynucleotide according to claim 2.

6. A host cell comprising the recombinant vector according to claim 3.

7. An isolated polynucleotide comprising a spliceosomal protein gene promoter of a plasmid in NCTC 12864 between an ATG codon at a start of a coding sequence and a PstI site 2.5 kb upstream of the ATG codon.

8. An isolated polynucleotide comprising a spliceosomal protein gene promoter of a plasmid in NCTC 12865 between an ATG codon at a start of a coding sequence and an EcoRI site 2 kb upstream of the ATG codon.

9. A recombinant expression control polynucleotide comprising a promoter selected from the group of plant spliceosomal protein gene promoters consisting of potato U1A promoter, potato U2B"_promoter, and maize PRP8 promoter.

10. A recombinant polynucleotide comprising the expression control polynucleotide according to claim 9 operably linked to a second polynucleotide.

11. The recombinant polynucleotide according to claim 10, wherein the second polynucleotide encodes a polypeptide.

12. The recombinant polynucleotide according to claim 10, wherein the second polynucleotide encodes a ribozyme.

13. The recombinant polynucleotide according to claim 10, wherein the second polynucleotide encodes anti-sense RNA.

14. A host cell comprising the recombinant polynucleotide according to claim 10.

15. A transgenic plant or the progeny or seeds thereof, comprising the recombinant polynucleotide according to claim 10.

16. A recombinant vector comprising the expression control polynucleotide according to claim 9.

17. A method for producing a recombinant vector, said method comprising ligating the expression control polynucleotide according to claim 9 to a vector.

18. A method for controlling the expression of a polypeptide from a polynucleotide encoding the polypeptide, said method comprising operably linking said polynucleotide to the expression control polynucleotide according to claim 9 and permitting expression of the polynucleotide encoding the polypeptide.

19. A recombinant polynucleotide comprising a sequence selected from the group consisting of SEQ ID No:1, SEQ ID No:2, SEQ ID No:3, and SEQ ID No4.

20. A recombinant polynucleotide comprising the polynucleotide according to claim 19, operably linked to a second polynucleotide.

21. The recombinant polynucleotide according to claim 20, wherein the second polynucleotide encodes a polypeptide.

22. The recombinant polynucleotide according to claim 20, wherein the second polynucleotide encodes a ribozyme.

23. The recombinant polynucleotide according to claim 20, wherein the second polynucleotide encodes anti-sense RNA.

24. A recombinant vector comprising at least one polynucleotide according to claim 19.

25. A host cell comprising the recombinant polynucleotide according to claim 20.

26. A transgenic plant or the progeny or seeds thereof, comprising the recombinant polynucleotide according to claim 20.

27. A method for producing a recombinant vector, said method comprising ligating the expression control polynucleotide according to claim 19 to a vector.

28. A method for controlling the expression of a polypeptide from a polynucleotide encoding the polypeptide, said method comprising operably linking said polynucleotide to the expression control polynucleotide according to claim 19 and permitting expression of the polypeptide encoded by said polynucleotide.

* * * * *